United States Patent [19]

Chandrasekaran

[11] 4,314,557

[45] Feb. 9, 1982

[54] DISSOLUTION CONTROLLED ACTIVE AGENT DISPENSER

[75] Inventor: Santosh K. Chandrasekaran, Palo Alto, Calif.

[73] Assignee: ALZA Corporation, Palo Alto, Calif.

[21] Appl. No.: 150,966

[22] Filed: May 19, 1980

[51] Int. Cl.³ .............................................. A61M 7/00
[52] U.S. Cl. ................................................... 128/260
[58] Field of Search .............. 128/127, 130, 155, 156, 128/260; 424/20, 22–23, 28, 32

[56] References Cited

U.S. PATENT DOCUMENTS

| | | | |
|---|---|---|---|
| 3,641,237 | 2/1972 | Gould et al. | 128/260 |
| 3,737,521 | 6/1973 | Born | 128/260 |
| 3,742,951 | 7/1973 | Zaffaroni | 128/260 |
| 3,892,842 | 7/1975 | Zaffaroni | 128/130 |
| 3,921,636 | 11/1975 | Zaffaroni | 128/130 |
| 3,926,188 | 12/1975 | Baker et al. | 128/260 |
| 3,948,254 | 4/1976 | Zaffaroni | 128/127 |
| 3,996,934 | 12/1976 | Zaffaroni | 128/130 |
| 4,016,251 | 4/1977 | Higuchi et al. | 128/130 |
| 4,060,084 | 11/1977 | Chandrasekaran | 128/260 |
| 4,177,256 | 12/1979 | Michaels et al. | 128/260 |

*Primary Examiner*—C. Fred Rosenbaum
*Attorney, Agent, or Firm*—Paul L. Sabatine; Edward L. Mandell; Michael A. Kondzella

[57] ABSTRACT

Drug dispensers comprising a flat body composed of a drug solute phase dispersed in a continuous polymer matrix phase in which the release rate of drug from the body is substantially constant and is controlled by the rate at which the drug solute phase dissolves in the continuous polymer matrix phase. Such control and constancy are realized by establishing specific correlations between the diffusion coefficient, dissolution rate constant, and thickness of the body.

7 Claims, 4 Drawing Figures

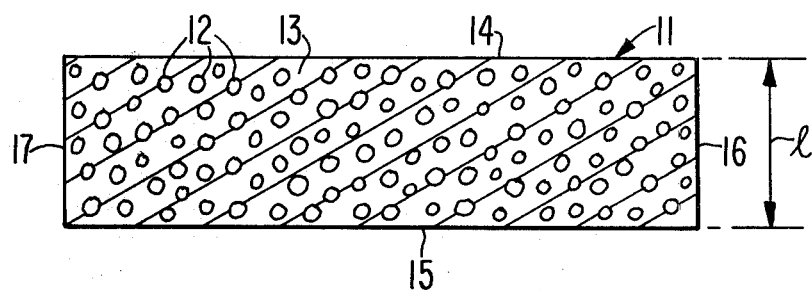
FIG. 1
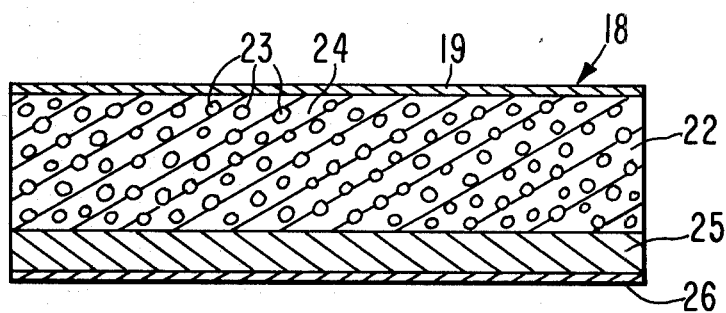
FIG. 2
FIG. 4
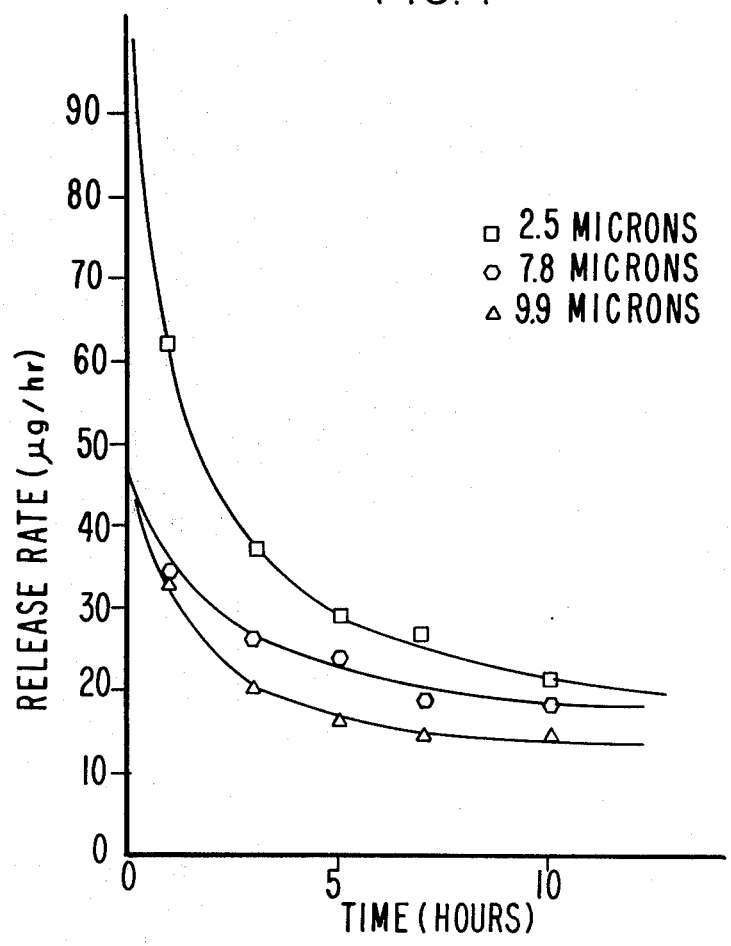

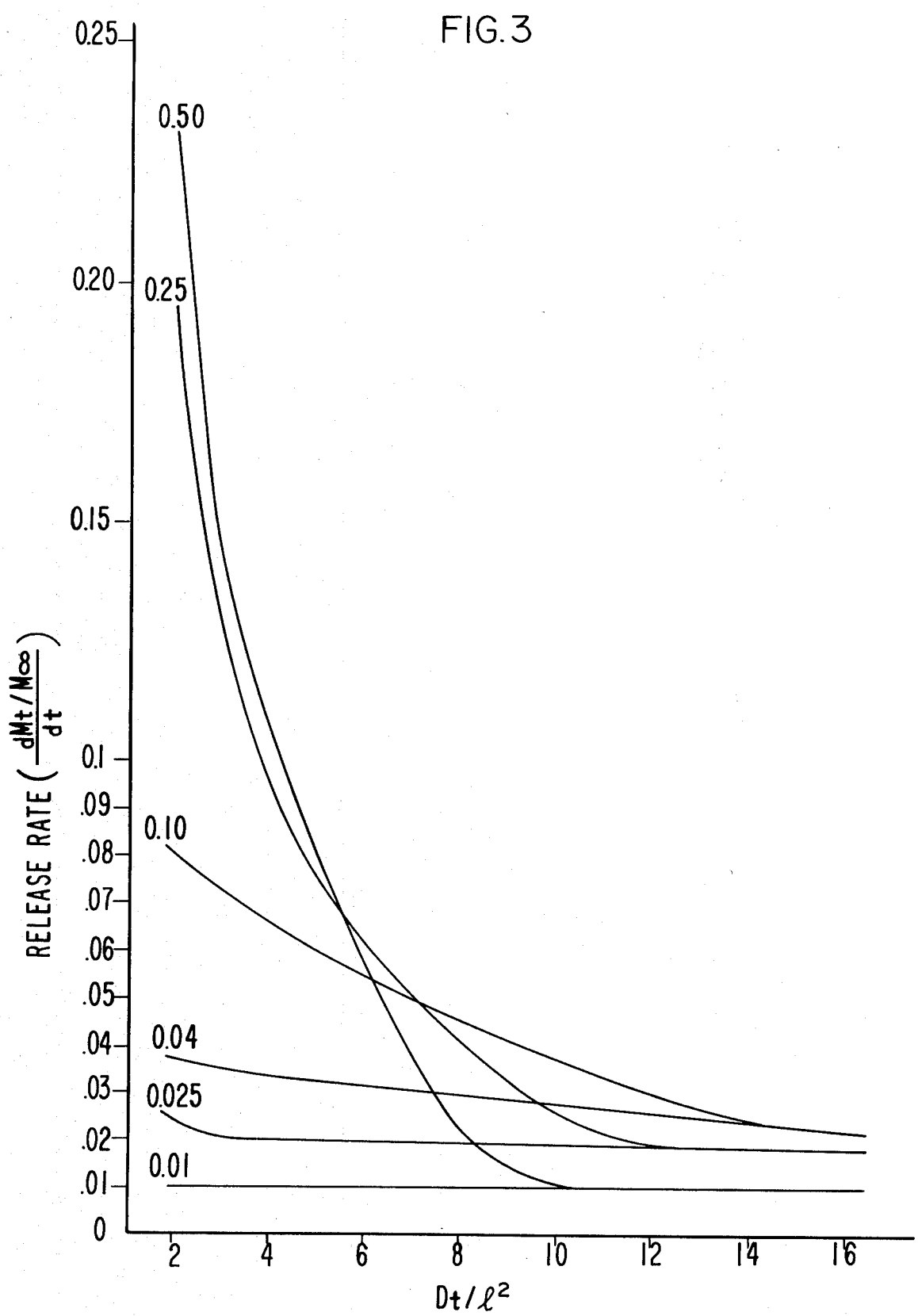

DISSOLUTION CONTROLLED ACTIVE AGENT DISPENSER

DESCRIPTION

1. Technical Field

The invention relates to a certain embodiment of an active agent dispenser composed of an active agent solute phase dispersed in a continuous matrix phase in which the rate at which the solute phase dissolves in the matrix phase controls the rate at which the active agent is released from the dispenser.

2. Background Art

Higuchi, J. Soc. Cosmet. Chem., 11, 85 (1960) first proposed the theory of diffusional release of a dispersed solute, such as a drug or other active agent, from a polymer matrix where the initial concentration of solute in the matrix is greater than its solubility in the matrix. Numerous sustained release drug formulations which follow Higuchi's theory are described in the pharmaceutical literature. The release rate of drug from such formulations is said to be controlled by the rate at which the drug diffuses through the matrix and to be inversely proportional to the square root of time.

There are reported instances where the release of dispersed drug from a continuous matrix did not follow the theory proposed by Higuchi. For instance Haleblain et al, J. Pharm. Sci. 60, 541 (1971) studied the in vitro release rate of steroids from silicone matrices and found their results were inconsistent with Higuchi's theory. The suggested explanation for the inconsistency was that dissolution rather than diffusion controlled the release rate. Similarly, Bottari et al, J. Pharm. Sci. 63, 1979, reported that the release rate of salicylic acid from ointment bases did not follow Higuchi's diffusion theory, and they related the discrepancy to an inadequate dissolution rate of the suspended particles.

Actually the above instances comport with accepted theory that the release rate of dispersed solute from a continuous polymer matrix is a complex function that involves both a diffusion component and a dissolution component. From such theory it would be expected that formulations of drug and polymer matrices may be made such that the rate at which the drug dissolves in the matrix is the controlling energy step. In such formulations diffusion of drug molecules in the matrix would be extremely fast relative to the solubilization of drug molecules in the matrix. What is not apparent, however, and what lies at the heart of the present invention, is the discovery that a substantially constant release rate of agent may be achieved by certain embodiments of such formulations.

DISCLOSURE OF INVENTION

The invention is an active agent dispenser consisting essentially of a flat body consisting essentially of a particulate active agent solute phase dispersed in a continuous matrix phase that is permeable to the active agent solute phase wherein the following conditions are met (a) $D >> K$ where D is the diffusion coefficient of the active agent solute phase in the matrix phase in $cm^2/sec$ and K is the dissolution rate constant of the active agent solute phase in the matrix phase in cm/sec and (b) $Kl/D$ is less than about 0.06 where K and D are as defined previously and l is the thickness of said body in cm.

When these conditions are met the rate at which active agent is released from these dispensers is controlled by the rate at which the active agent solute phase dissolves in the matrix phase and the rate of release is substantially constant over a substantial portion of the time over which active agent is dispensed.

BRIEF DESCRIPTION OF DRAWINGS

In the drawings, which are not to scale:

FIG. 1 is a sectional view of one embodiment of the invention;

FIG. 2 is a sectional view of another embodiment of the invention;

FIG. 3 is a graph that shows the validity of condition (b) above; and

FIG. 4 is a graph of release rate versus time for the dispensers described in the examples, infra.

DESCRIPTION OF EMBODIMENTS OF INVENTION

FIG. 1 depicts a simple embodiment of the invention such as might be used to administer drug within body cavities of humans and other warm blooded animals. That embodiment is in the form of a solid flat body 11 composed of a homogeneous dispersion of drug particles 12 in a continuous matrix 13 that is permeable to the drug. Matrix 13 is "continuous" in the sense that it encapsulates the particles of drug without significant particle-to-particle contact and forms a cohesive stable mass in which the particles are dispersed. In this regard such conditions usually cannot be achieved if the drug constitutes more than about 35% by volume of the dispersion. The concentration of drug in the matrix is such that the matrix is saturated with drug over the lifetime of the dispenser. In other words, excess drug is present in the matrix. Usually the drug will constitute from 5% to 25% by volume of the body. Although particles 12 are represented as spheres for the purpose of illustration, it will be understood that depending upon the drug involved and the manner in which the drug was put into particulate form the particles may have various regular or irregular geometric configurations. The particles are preferably substantially nonaggregated in the matrix. The particle size of the solute phase is an important parameter in the invention because the dissolution rate content, K, is directly proportional to the surface area of the solute. Thus, K may be varied by varying the particle size of the solute. In drug dispensers the average particle size (as determined by the BET absorption technique) will usually be in the range of 1 to 50 microns.

Drug 12 should have a low water solubility. Low water solubility is a requirement so that the drug does not function to any significant extent as an osmotically effective solute that would imbibe water from the environment into body 11. The degree of water solubility will depend somewhat on the permeability of matrix 13 to water. If the matrix has a high permeability to water, the water solubility of the drug should be very low. Correspondingly, if the matrix is impermeable to water, a more soluble drug may be used. In most instances the drug will be less than 40% by weight soluble in water. The drug will also typically be nonionic since in most instances the matrix will be made from a polymer, and most polymers are impermeable to ionic species. The pharmacologic nature of the drug will depend upon the therapy for which body 11 is intended. Drugs that produce either a local effect at the administration site or a systemic effect at a remote site may be used in the invention. Examples of nonionic drugs that may be used in the invention are disclosed in U.S. Pat. No. 3,926,188.

Matrix 13 will usually be made from a solid or semi-solid (gel) polymer composition. The diffusion coefficient (D) of matrix 13 to drug 12 will typically be in the range of $10^{-7}$ to $10^{-12}$ cm$^2$/sec and will also typically be at least 10 times greater than K. The particular polymer composition used in a given embodiment will depend upon the drug involved and the required release rate of drug to achieve therapy. Basically the polymer compositions will be matched with drugs such that the values of D and K are able to fit the above mentioned conditions. Examples of polymers that may be used as matrix materials in the invention are silicone rubber, polyisoprene polyisobutylene, ethylene-vinyl acetate copolymer polypropylene, polycarbonate and polymethylmethacrylate.

As indicated above body 11 is flat. This means that its major surfaces, designated 14, 15 in FIG. 1 are essentially parallel and are distinctly greater than its minor surfaces, designated 16, 17 in FIG. 1. The thickness, l, of body 11 is an important parameter in one of the above conditions. In drug dispensing embodiments such as that of FIG. 1, the thickness will usually be in the range of 50 to 1,500 microns (0.005 to 0.15 cm).

FIG. 2 depicts another embodiment of the invention, generally designated 18, in the form of a bandage for administering a drug to the skin. FIG. 2 shows bandage 18 before it is applied to the skin. The components of bandage 18 are, from the top, a drug impermeable backing layer 19, a drug reservoir layer 22 composed of a homogeneous dispersion of drug particles 23 in a continuous matrix 24, a contact adhesive layer 25, and a strippable coating layer 26. Layer 22 is in effect a drug dispenser identical in structure and operation to monolithic body 11 of FIG. 1. Accordingly drug 23 and matrix 24 are selected using the criteria discussed above with respect to drug 12 and matrix 13 of body 11. The other components of bandage 18 are merely accessory elements that permit layer 22 to be easily and effectively administered to the skin. They do not interact with layer 22 and do not alter its function. Backing layer 19 serves as a protective overlay and prevents drug from being released via the top surface of layer 22. Contact adhesive layer 25 serves as the means by which bandage 18 is affixed to the skin. It is passive with respect to the release rate of drug. As such, it must be highly permeable to the drug so that the drug passes rapidly through it from the lower surface of reservoir layer 22 to the skin surface. Strippable coating layer 26 merely serves as a protective underlay for layer 25 and is removed before bandage 18 is placed on the skin. Materials for making backing layer 19, contact adhesive layer 25 and strippable coating layer 26 are disclosed in U.S. Pat. No. 4,060,084.

Conditions (a) and (b) above are essential requirements in the present invention. Condition (a) must be met for the solubilization of the drug in the matrix to be the step or act that controls that rate at which drug is released from the dispenser. Condition (b) must be met in order for the release rate to be substantially constant. FIG. 3 verifies the criticality of condition (b). It is a plot of the release rate of solute for various assumed values of the dimensionless expression lK/D as a function of the dimensionless expression D t/l$^2$, where l,K and D are as defined previously and t represents time. The values for lK/D are indicated at the head of each curve in FIG. 3. The curves shown in FIG. 3 were determined from the equation for the release rate of solute from a plane sheet of a solute-matrix mixture. That equation was derived from the differential equation that mathematically expresses the mass transport process in such a sheet. As shown, at lK/D values below about 0.06 the release rate is substantially independent of time whereas at values above about 0.06 the release rate varies significantly with time.

Known procedures are available for determining K and D for any given solute-matrix system. See for instance J. Crank and G. S. Park, "Diffusion in Polymers", Academic Press, NY (1968).

The dispensers of the invention are further described by the following examples. These examples are not intended to limit the invention in any manner. Unless indicated otherwise, proportions are by weight.

Drug dispensers in the form of monolithic flat bodies of a drug solute phase dispersed in a continuous polymeric matrix phase were made as follows. One part of polyisobutene (mw 1,500,000) and 1.25 parts polyisobutene (mw 35,000) and 2 parts of mineral oil (8 cs) were dissolved in heptane at room temperature. Clonidine was added in three different average particle sizes, 2.5, 7.8, and 9.9 microns (particle sizes were determined by specific surface area analysis using a gas absorption (BET) technique) to three separate portions of the resulting solution so as to obtain a total solids content of about 25% in each portion. At that concentration the portions had a suitable viscosity to permit them to be cast onto a polyester substrate using a gardner knife apparatus. The cast films were allowed to set at room temperature and were then oven dried at 50° C. to remove residual heptane. The thickness of each dried film was about 65 microns. D for each film was $2.3 \times 10^{-8}$ cm$^2$/sec. K values for the three films were, respectively, $30 \times 10^{-8}$ cm/sec, $23 \times 10^{-8}$ cm/sec, and $20 \times 10^{-8}$ cm/sec. Correspondingly lK/D for the three films were 0.08, 0.06, and 0.05 respectively.

The in vitro release rate of drug from each of the three films into water at 32° C. was determined by a standard release rates test procedure. Drug concentrations in the water were determined chromatographically. The results of those tests are shown graphically in FIG. 4. As shown, the release rates of drug from the 2.5 micron particle size film varied substantially with time whereas the release rates from the 7.8 and 9.4 micron particle size films were substantially constant.

Modifications of the invention dispensers described above that are equivalent in structure and function thereto to those of skill in the pharmaceutical art are intended to be within the scope of the following claims.

I claim:

1. An active agent dispenser consisting essentially of a flat body consisting essentially of a particulate active agent solute phase dispersed in a continuous matrix phase that is permeable to the active agent solute phase wherein the following conditions are met
   (a) D>>K where D is the diffusion coefficient of the active agent solute phase in the matrix phase in cm$^2$/sec and K is the dissolution rate constant of the active agent solute phase in the matrix phase in cm/sec and
   (b) Kl/D is less than about 0.06 where K and D are as defined previously and l is the thickness of said body in cm whereby the rate at which active agent is dispensed is (i) controlled by the rate at which the active agent solute phase dissolves in the matrix phase, and (ii) substantially constant.

2. The dispenser of claim 1 wherein the agent, is a drug, D is in the range of $10^{-7}$ to $10^{-12}$ cm$^2$/sec and is at least 10 times greater than K, and l is in the range of 50 to 1500 microns.

3. The dispenser of claim 2 wherein the continuous matrix phase is a polymer selected from the group consisting of silicone rubber, polyisoprene, polyisobutylene, ethylenevinylacetate copolymer, polypropylene, polycarbonate, and polymethylmethacrylate.

4. A drug dispenser in the form of a bandage for administering drugs to the skin comprising:
   (a) a drug impermeable backing layer forming the top of the bandage.
   (b) a drug reservoir layer adjacent and below the backing layer consisting essentially of a particulate drug solute phase dispersed in a continuous matrix phase that is permeable to the drug solute phase wherein the following conditions are met:
      (i) $D \gg K$ where D is the diffusion coefficient of the drug solute phase in the matrix phase in cm$^2$/sec and K is the dissolution rate constant of the drug solute phase in the matrix phase in cm/sec and
      (ii) Kl/D is less than about 0.06 where K and D are as defined previously and l is the thickness of the drug reservoir layer in cm, and
   (c) means for affixing the bandage to the skin.

5. The drug dispenser of claim 4 wherein the means for affixing the bandage to the skin is a contact adhesive layer adjacent and below the drug reservoir layer, said contact adhesive layer being permeable to the drug and forming the basal surface of the bandage.

6. The drug dispenser of claim 5 wherein D is in the range of $10^{-7}$ to $10^{-12}$ cm$^2$/sec and is at least 10 times greater than K, and l is in the range of 50 to 1500 microns.

7. The drug dispenser of claim 5 wherein the matrix phase is a polymer selected from the group consisting of silicone rubber, polyisoprene, polyisobutylene, ethylene-vinyl acetate copolymer, polypropylene, polycarbonate, and polymethylmethacrylate.

* * * * *